US005543016A

United States Patent [19]

Fehlner et al.

[11] Patent Number: 5,543,016
[45] Date of Patent: Aug. 6, 1996

[54] PHOTOCONVERSION OF STEROIDS IN MICROREACTORS

[75] Inventors: James R. Fehlner, Salem Township, Pa.; Dow Firnberg, Creskill, N.J.

[73] Assignee: Inrad, Northvale, N.J.

[21] Appl. No.: 884,447

[22] Filed: May 18, 1992

Related U.S. Application Data

[63] Continuation-in-part of Ser. No. 728,880, Jul. 12, 1991, Pat. No. 5,374,405, and a continuation-in-part of Ser. No. 864,814, Mar. 31, 1992, Pat. No. 5,474,681.

[51] Int. Cl.[6] .................................................. C07B 61/00
[52] U.S. Cl. ................................ 204/157.6; 204/157.15; 204/157.67
[58] Field of Search ........................... 204/157.15, 157.6, 204/157.67

[56] References Cited

U.S. PATENT DOCUMENTS

| | | | |
|---|---|---|---|
| 3,838,029 | 9/1974 | Fischer | 204/157.67 |
| 3,929,770 | 12/1975 | Ishikawa et al. | 204/157.67 |
| 4,265,822 | 5/1981 | Deluca et al. | 204/157.67 |
| 4,388,242 | 6/1983 | Malatesta et al. | 260/397.2 |
| 4,551,214 | 11/1985 | Hansen et al. | 204/157.67 |
| 4,609,444 | 9/1986 | Guillet | 204/157.6 |
| 4,686,023 | 8/1987 | Stevens | 204/157.67 |
| 4,937,292 | 6/1990 | Slemon | 525/326.8 |
| 5,035,783 | 7/1991 | Goethals et al. | 204/157.67 |
| 5,252,191 | 10/1993 | Pauli et al. | 204/157.67 |

FOREIGN PATENT DOCUMENTS 1248907  1/1989  Canada .

OTHER PUBLICATIONS

Facaha et al., "Surface Photochem . . . ".

F. Boomsma, et al., The "Overirradiation products" of Previtamin D and Tachysterol: Toxisterols[1-3]; *Journal of the Royal Netherlands Chemical Society*, Apr. 1977, vol. 96(4), pp. 104–112.

O. A. de Bruin, et al., Retro–steriod –A New Class of Compounds with Sex–hormone Action, *Philips Technical Review*, vol. 28, pp. 70–79.

William S. Allen, et al., Steroidal Cyclic Ketals. XI. The Conversion of 11–epi–Hydrocortisone into Hydrocortisone, vol. 76, Dec. 5, 1954, pp. 6116–6119.

M. P. Rappoldt, et al., Investigations on Sterols XXXVII –New Routes to 9,10–isomers of 6–dehydroprogesteron, *Recueil*, vol. 90 (1971), pp. 27–32.

R. Antonucci, et al., $\Delta^{5,7}$–Steroids, XIII, Steroidal Cyclic Ketals. II[1,2] The Preparation of $\Delta^{4,7}$–Pregnadiene–3, 20–Dione and $\Delta_{4,7}$–Pregnadiene–21–OL–3,20–Dione–Acetate, *Journal of Organic Chemistry*, vol. 17, pp. 1369–1374 (1952).

R. M. Moriarty, et al., Formation of Vitamin $D_3$ in Synthetic Lipid Multibilayers. A Model for Epidermal Photosynthesis, *Journal of the American Chemical Society*, Jun., 1980, vol. 102:12, pp. 4257–4259, Jun. 1980.

V. Malatesta, et al., Laser Photochemical Production of Vitamin $D^1$, *Journal of the American Chemical Society*, vol. 103, pp. 6781–6783 (1981).

W. G. Dauben, Wavelength–Controlled Production of Previtamin $D_3$, *Journal of the American Chemical Society*, vol. 104, pp. 355–356 (1982).

(List continued on next page.)

*Primary Examiner*—John Niebling
*Assistant Examiner*—C. Delacroix-Muirheid
*Attorney, Agent, or Firm*—Stroock & Stroock & Lavan

[57] ABSTRACT

The photoconversion of steroids is carried out in microreactors to yield desired products, while limiting the formation of undesirable byproducts. The steroid reactant is combined with a microreactor such as solid particles having controlled spaces of appropriate size to provide stereochemical control over the reaction. Appropriate catalyst particles include silica and zeolitic material. The reaction can be conducted in a fluidized bed reactor and the formation of undesirable byproducts can be effectively limited.

27 Claims, 5 Drawing Sheets

OTHER PUBLICATIONS

Rajeev Farwaha, et al., Surface Photochemistry: Enone Photocycloaddition by Absorbed Molecules on Silica Gel and Alumina[1], *Journal of Organic Chemistry*, vol. 50, No. 2, 245–250 (1985).

D. H. R. Barton, A Convenient Synthesis of 1α-Hydroxy–Vitamin $D_3$, *Journal of the American Chemical Society*, vol. 95:8, pp. 2748–2749 (Apr. 1973).

M. Fischer, Industrial Applications of Photochemical Synthesis, *Angew. Chem. Int. Ed. Engl.*, vol. 17, pp. 16–26 (1978).

K. Takada, et al., Isolation and Identification of Tachysterol$_3$ in Rat Skin Exposed to Ultraviolet Light, *Biochimica et. Biophysica Acta*, 666 (1981), pp. 356–360.

*Chemical Abstracts Service*, Search on Vitamin $D_3$ 1α–Hydroxy Vitamin $D_3$ Photochemical Synthesis –31 references.

PHOTOCONVERSION OF STEROIDS IN MICROREACTORS

CROSS-REFERENCE TO RELATED APPLICATION

This application is a continuation-in-part of U.S. patent application Ser. No. 07/728,880, filed Jul. 12, 1991, now U.S. Pat. No. 5,374,405, and Ser. No. 07/864,814, filed Mar. 31, 1992, now U.S. Pat. No. 5,474,681.

BACKGROUND OF THE INVENTION

The invention relates generally to the photoconversion of steroids on solid catalytic surfaces and more particularly to controlling the stereochemistry of the photoconversion reaction by proper selection of a microreactor.

Photochemical isomerization of steroids are important in the industrial synthesis of commercial products. For example, the photoisomerization of 7-dehydrocholesterol (7-DHC) yields previtamin $D_3$, which can be converted by conventional methods, such as by thermal rearrangement, to vitamin $D_3$. Vitamin $D_3$ has many important uses. For example, vitamin $D_3$ can be used as an additive to milk and in animal feeds to prevent rickets.

A similar type of photoisomerization is carried out to produce $1\alpha,25$-dehydroxyvitamin $D_3$. This is the actual active form of vitamin $D_3$ that is responsible for regulating calcium metabolism. The synthesis of dydrogesterone, developed by Philips-Duphar, also includes a photoisomerization of a steroidal intermediate. (M. Fischer, Angew. Chem. Int. Ed. Engl. 17, 16–26 (1978).)

The photoisomerization of steroids is conventionally carried out in solution. The conventional photolysis of 7-dehydrocholesterol initially gives the desired previtamin $D_3$. However, previtamin $D_3$ also absorbs light of the same region of the electromagnetic spectrum as does 7-dehydrocholesterol. This leads to a second undesirable photo-induced isomerization in which tachysterol is formed.

There have been many attempts to deal with the unwanted formation of tachysterol. However, these attempts have been less than completely satisfactory. For example, one approach is to stop irradiation after 30–50% conversion to previtamin $D_3$ and then isolate previtamin $D_3$. However, this procedure adds considerable expense to the production of vitamin $D_3$.

Another approach is to use consecutive irradiations with different wavelengths. An initial high energy irradiation of 7-dehydrocholesterol gives a mixture of previtamin $D_3$ and tachysterol. A second lower energy radiation then converts some of the tachysterol back to previtamin $D_3$. This is also not fully satisfactory and leads to a higher percentage of lumisterol in the product (V. Malatesta, C. Willis and P. A. Hackett, *J. Am. Chem. Soc.*, 103, 6781–2–3, (1981) and U.S. Pat. No. 4,388,242). The contents of U.S. Pat. No. 4,388,242 are incorporated herein, by reference.

Still another approach includes the addition of xanthenone analog sensitizers to the steroidal reactant, followed by irradiation with low energy wavelength light. This leads to decreased amounts of tachysterol in the product mixture (H. J. Hansen and K. Pfoertner, European Patent 130509, 1985). A second irradiation at lower energy with anthracene as an initiator also minimizes the amount of tachysterol present in the reaction mixture (See, U.S. Pat. No. 4,686,023, the contents of which are incorporated herein by reference). However, the use of sensitizers and initiators are generally undesirable because they complicate the purification process.

Accordingly, it is desirable to provide an improved method of conducting photoconversion reactions of steroids with greater control of the reaction product.

SUMMARY OF THE INVENTION

Generally speaking in accordance with the invention, a method of conducting the photoconversion of steroids in microreactors into desired products, while limiting the formation of undesirable byproducts is provided. The steroid reactant is introduced into a microreactor, such as the controlled spaces of solid catalyst particles having pores, channels or chambers of appropriate size to provide stereochemical control over the reaction. Appropriate catalyst particles include silica material and zeolitic material. The reaction is preferably conducted in a fluidized bed reactor and the formation of undesirable byproducts can be effectively limited.

Accordingly, it is an object of the invention to provide an improved method of conducting the photoconversion of steroids.

Another object of the invention is to provide a method of limiting the amount of undesirable byproducts formed when photoconversions are conducted.

A further object of the invention is to provide a method of conducting the photoconversion of steroids in a simpler manner with less waste and fewer purification steps.

Yet another object of the invention is to provide an improved method of synthesizing vitamin D.

Still other objects and advantages of the invention will in part be obvious and will in part be apparent from the specification and drawings.

The invention accordingly comprises the several steps and the relation of one or more of such steps with respect to each of the others, and the apparatus embodying features of construction, combinations of elements and arrangements of parts which are adapted to effect such steps, all as exemplified in the following detailed disclosure, and the scope of the invention will be indicated in the claims.

BRIEF DESCRIPTION OF THE DRAWINGS

For a fuller understanding of the invention, reference is had to the following description taken in connection with the accompanying drawings, in which.

DETAILED DESCRIPTION OF THE PREFERRED EMBODIMENTS

Figure 1:
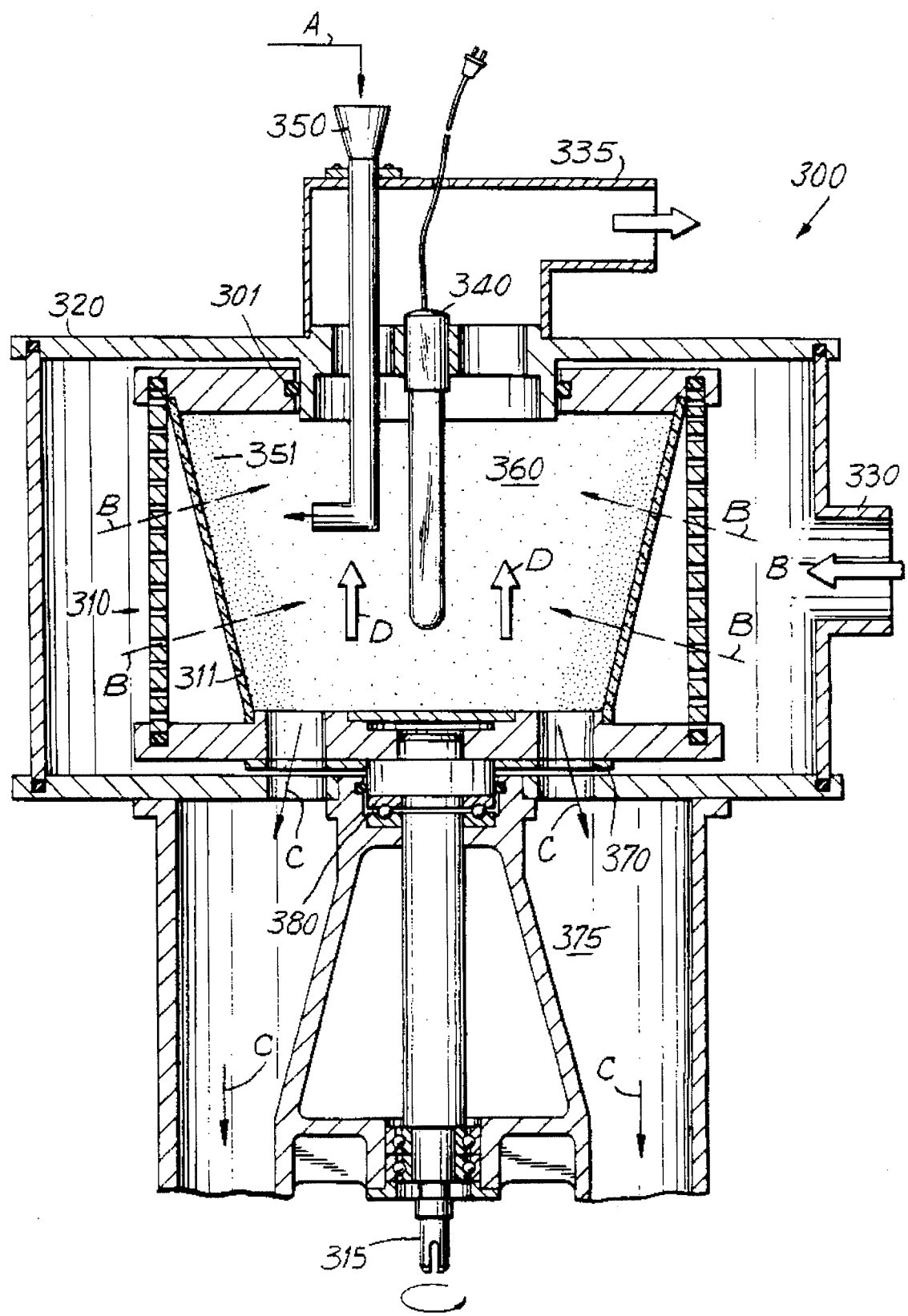
FIG. 1 is a front cross-sectional view of a continuous feed rotating fluidized bed reactor in accordance with an embodiment of the invention.

A process is provided whereby steroidal compounds can be converted to desired products with increased stereochemical control compared to conventional processes. This is accomplished by restricting the reaction environment of the molecule being reacted to prevent the formation of undesirable side products which will have acceptably low rates of formation within the controlled reaction environment. Control of byproducts can be accomplished by controlling the spacial environment of the reaction so that the resultant product molecule cannot rearrange to an isomer that requires a larger space, and/or by bonding the desired product molecule to groups on the surface of the solid to minimize conversion of the desired product to another isomer.

The photoreaction of molecules in controlled spaces can help direct the stereochemistry of the chemical reaction. Examples of these controlled spaces, which can be referred to as microreactors, include micelles, cyclodextrins, surface pores in materials such as silica and in the channels and chambers of zeolites. As used herein, the term "controlled spaces" in solids will include pores, channels and chambers.

The cycloaddition of testosterone proprionate to ethylene on silica gel has been shown to give preferential attack on the beta face, while in solvents such as methanol and ethyl acetate, the attack is preferentially on the alpha face. Photolysis on silica gel essentially eliminates the formation of the trans isomer which is observed in the solution photolysis. Therefore, the inversion required to obtain the trans form is disfavored on silica gel as well as at low temperatures in solvents. The effect is even more pronounced on alumina. These results are attributed to the adsorption of the steroid on the silica gel with the less hindered face down. This allows the strongest bonding between the carbonyl oxygen and the free OH's on the silica surface. However, this type of reaction control does not rely on the presence of reactant within a micro reactor and does not depend on the size of pores or other controlled spaces. For further details, see R. Farwaha, P. deMayo, J. H. Schauble and Y. C. Toong, J. Org. Chem., 50, 245–50 (1985), the contents of which are incorporated herein by reference.

The instant invention contemplates a number of different types of microreactors which can control the stereochemical outcome of the reaction in accordance with the invention. A first microreactor is the pores on the surface of silica gel or similar materials made from aluminum, titanium or other materials. Silica gel is silicon dioxide in an amorphous structure. Gel particles can be formed with a surface pocked with pores. These pores can range in sizes of from about 10 to several hundred angstroms. In addition, the surface is covered with Si—O—H groups which can readily form hydrogen bonds and dipole-dipole interactions with adsorbed molecules.

Another type of microreactor is the molecular sized controlled space openings in inorganic crystals such as zeolites. Zeolites are crystalline mixtures of silicon oxide and aluminum oxide and have open spaces within the crystal lattice due to the arrangement of the atoms. The crystal structure has differently sized metal oxygen rings. These can be eight, ten, twelve or larger membered rings. The arrangement of these rings can lead to the occurrence of channels and chambers within the zeolite crystal. The size of the channels and chambers in a zeolite crystal are generally uniform, while the size of pores in silica generally have a wide variation in sizes.

The Si:Al ratio in zeolites can vary from around 1:1 to greater than 2000:1. The zeolites with chambers, (for example Y and A zeolites) generally have lower Si:Al ratios, while those with channels (for example mordenite and ZSM-5 zeolites) have higher Si:Al ratios. The size of the channels and chambers can typically vary from about 4 to 15 angstroms or larger. These sizes are in the range of the size of organic molecules with long chain alkanes fitting in the smaller channels while larger molecules, such as steroids, require the larger diameter pores. In general, the controlled spaces should be larger than about 7 angstroms for most desired products.

Another type of microreactor is micelles formed when surfactants are dispersed in $H_2O$. These are typically in the form of fine oily droplets with an ionic surface dispersed in water. The reactants are hydrophobic and will stay within the droplet. By controlling the size of the droplet, the size of the microreactor can be controlled. In general, droplet sizes of less than 60 angstroms, preferably less than 30 angstroms are acceptable.

When conducting reactions in accordance with the invention, a steroidal reactant molecule, such as 7-dehydrocholesterol, can be loaded onto a solid substrate from a solvent, such as a hydrocarbon solvent, such as pentane. The solid, loaded with reactant, is then irradiated with light of an appropriate wavelength for conducting the reaction. One way of exposing the solid to the light is in a fluidized bed. If this approach is adopted, it is preferred that the reaction be run in an inert atmosphere to avoid the interference of oxygen with the intermediates. Therefore, preferred fluidizing gases include nitrogen and argon. The product can be removed from the solid with organic solvents.

One type of fluidized bed reactor that is particularly well suited for conducting the photochemical conversions in accordance with the invention is a rotating fluidized bed chemical reactor. Such a reactor is described in greater detail in co-pending U.S. Ser. No. 07/728,880, filed Jul. 12, 1991, the contents of which are incorporated herein by reference. A rotating fluidized bed reactor includes a bed vessel drum that can rotate and force particles of the bed against the drum wall. Accordingly, the central core at the axis of rotation will lack particles which will all be pushed against the outside drum wall. The drum (bed vessel) wall acts as a diffuser or distributor for the fluidizing gas and can be porous, perforotated, sceen-like, etc. The bed vessel wall is preferably cylindrical and vertical or inclined to promote particles traveling up the sides of the vessel wall. The bed vessel can be rotated by coupling a shaft to the bottom or top of the drum, with gears, with a chain wheel and drive chain, with a belt and the like. Although rotation rates will vary with the size of the reactor, gas flow rates and particle sizes, rotation rates of 200 to 1,000 rpm are preferred with rates of 400 to 700 rpm even more preferred.

The drum is preferably located within a plenum vessel and gas should be introduced from the side of the plenum vessel and tangentially to the bed wall of the drum. The gas can enter either with the direction of drum rotation or against the direction of drum rotation, depending on the intended application of the reactor. The top or bottom of the bed vessel should be coupled to a gas outlet and the gas can be recycled or processed further, depending on the type of reaction involved. Because of the strong centrifugal forces pushing the particles against the drum wall, the particles will not become entrained in the fluidizing gas flow.

A source of electromagnetic radiation, such as a UV lamp, can be included within the rotating bed vessel. The solid particles will not contact the light source which may not be protected with transparent shielding. The reaction can be run as a batch process or a continuous flow process, with particles being continuously added to and removed from the bed and recycled.

The reactor includes a rotating porous bed vessel drum within a plenum vessel. The drum rotates to hold the solid particles to sides thereof. Gas is introduced through the walls of the drum and can be drawn off at the top or bottom.

A continuous feed rotating fluidized bed photochemical reactor 300, in accordance with an embodiment of the invention is shown in FIG. 1. Reactor 300 includes a gas inlet pipe 330, a plenum vessel 320 and an exhaust 335. Fluidizing gas enters through inlet pipe 330, is distributed by plenum vessel 320 and exits through exhaust 335.

Reactor 300 also includes a UV lamp 340 for illuminating the bed, a drive shaft 315 for rotating the bed and a plurality of seals 301 to prevent gas leakage. The broken arrows shown in FIG. 1 show the direction of gas flow. The solid arrows show the direction of the flow of solids. A continuous flow of solid particles 351, that can include reactant for the fluidized bed are introduced at the top of the rotating bed through a particle feed nozzle 350 in the direction of an arrow A. Reactor 300 includes a cone shaped bed vessel drum 310 that has in inclined side wall 311. Inclined wall 311 of drum 310 makes it easier for solids 351 in drum 310 to travel up the sides of drum 310, when drive shaft 315 is rotated, than if side walls 311 were vertical. Wall 311 of drum 310 is porous and gas enters the bed therethrough in the direction of the plurality of arrows B.

During operation of continuous feed reactors 300, solids 351 are continuously added to drums 310 through particle feed nozzle 350 and exit through one or more adjustable discharging ports 370 in the direction of an Arrow C, into a collecting chamber 375. Reactor 300 should include a plurality of appropriate bearings and seals 380 in order to prevent any loss of gas or solid. Exhaust gases exit in the direction of a plurality of arrows D and can be recycled or otherwise processed.

When forming previtamin $D_3$, upon exposure of the sample to long wave UV light in the range of from 200 to 300 nm, the 7-dehydrocholesterol molecules are induced to undergo a ring opening to previtamin $D_3$. On further exposure, more of 7-dehydrocholesterol is converted to previtamin $D_3$, but the previtamin $D_3$ remains unchanged. At this point the organic products can be extracted from the solid substrate and previtamin $D_3$ can be converted to vitamin $D_3$ using conventional thermal technology in solution. Alternatively, the substrate can be heated in the fluidized bed and previtamin $D_3$ will be converted into vitamin $D_3$ while still on the substrate. At that point, the organic products can be extracted from the solid substrate and purified.

Steroids are any of a considerable number of organic compounds having a documented polycyclic 17-carbon phenanthrene nucleus. The carbons are numbered 1 through 17 and the bonds between the carbons, such as between the number 2 and number 3 carbons, are commonly referred to as the 2, 3 bond. Steroids include monohydric alcohols, also referred to as sterols (such as cholesterol), hormones (such as cortisone) and previtamins (such as ergosterol).

The preferred steroidal structures for the starting materials in accordance with the invention have double bonds across the 5,6 and 7,8 bonds in the B ring of the compound. In addition, there may be an oxygen group on the 3 position of the A ring as well as substituents on other positions. Examples of these types of compounds used in commercial or proposed commercial processes include 7-dehydrocholesterol and 1-hydroxy- 7-dehydrocholesterol diacetate and 4,7 pregnadiene- 3,18-dione diethyleneketal. The methods described herein are particularly well suited for forming the various forms of vitamin D.

In the practice of the invention, solid catalyst materials (such as silica) can be dry or if desired, loaded with water to decrease the hydroscopic nature of the solid material. If a fluidized bed is used, humidified fluidizing gas can be passed through the bed to add water to the bed particles. The addition of water to the absorbent solid is particularly useful if there is a potential that the solid will dehydrate the organic species. For example, 7-dehydrocholesterol is easily dehydrated to yield undesirable side products. For preferred results, the silica should have about 5–35% water, preferably 10–30%. If zeolite catalysts are used, it is preferred that zeolites come to equilibrium with water in the air before being used.

The reactions in accordance with the invention are preferably carried out at a temperature range of from −30° C. to 30° C., more preferably between 0° and 20° C. The reaction conditions can also be varied to carry out thermally initiated reactions in the overall process. If a fluidized bed is used, the temperature of the fluidizing gas can be varied to control the reaction temperature. The reactant is preferably irradiated with light having a wavelength in the range of from 200 to 700 μm, more preferably between 200 to 300 μm. However, the specific wavelength requirements of a particular reaction will vary.

The solid catalyst particle size will preferably range from 0.1 to 500 microns and will be more preferably in the range of from 1 to 200 microns. In general, the reaction space of the microreactor should be less than about 30 Å in diameter. When zeolites are used, especially in the formation of vitamin D, they should be chosen to have channels having a pore size of 5 to 10 Å and more preferably 6 to 8 angstroms in diameter. Alternatively, the zeolites can have chambers ranging from 10 to 20 Å, more preferably 12 to 16 angstroms in diameter. If silica gel is chosen, the pores should be from 10 to 50 Å, more preferably 20 to 30 angstroms in size. A more detailed discussion of zeolite catalysts can be found in copending U.S. Ser. No. 07/864,814, filed Mar. 31, 1992, the contents of which are incorporated herein by reference.

It is also preferred that the zeolite catalysts are in the "neutral forms." Where there is an aluminum atom in the zeolite framework, there is a net negative charge. To compensate for this, there must be a corresponding positively charged ion (cation). These cations can be hydrogen ions and in that case, the zeolites are referred to as being in the acid form. If the cations are metal ions, commonly alkali metal ions such as sodium, the zeolites are referred to as being in the "neutral" form. The size of the cations may allow fine tuning of stereocontrol of the reaction.

For organic compounds that can undergo acid catalyzed reactions such as rearrangement or dehydration it is preferred that the neutral form is used. The specific metal cation to be used depends on the desired space restrictions. Large cations such as rubidium or sodium can be used when small cavities are desired and smaller ions, such as lithium or sodium for larger volume cavities.

Preferred embodiments of the invention will be described with greater particularity with reference to the following examples. These examples are provided for purposes of illustration only and are not intended to be construed in a limiting sense.

EXAMPLE 1 FOR COMPARISON

Figure 2:
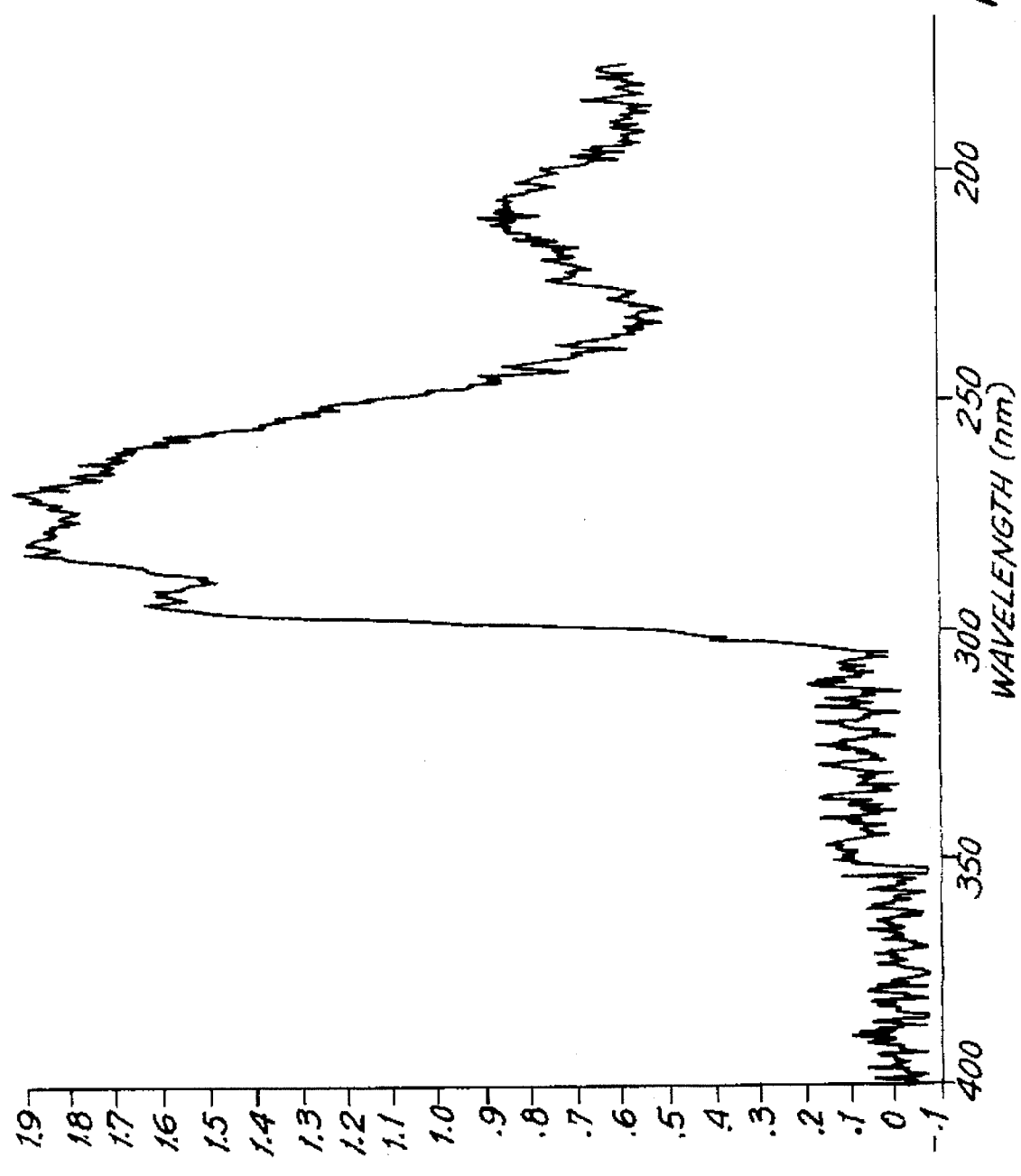
FIG. 2 is a spectral analysis of a solution of 7-DHC.

To confirm the results reported in the literature for the conventional solution photolysis of 7-dehydrocholesterol, a hexane solution of 0.0090 g of 7-dehydrocholesterol in 250.0 ml of hexane was prepared. A portion of the solution was placed in a quartz curvet and a UV spectrum was taken over the range of 400 to 200 nm. The resulting spectrum, shown in FIG. 2, was the same as that reported in the literature, with several peaks between 300 and 260 nm. The sample was then exposed to light from a low pressure mercury lamp for a measured period of time. Any hexane lost by evaporation during exposure was replaced to maintain constant concentration. After each exposure, another UV spectrum was taken.

Figure 3:
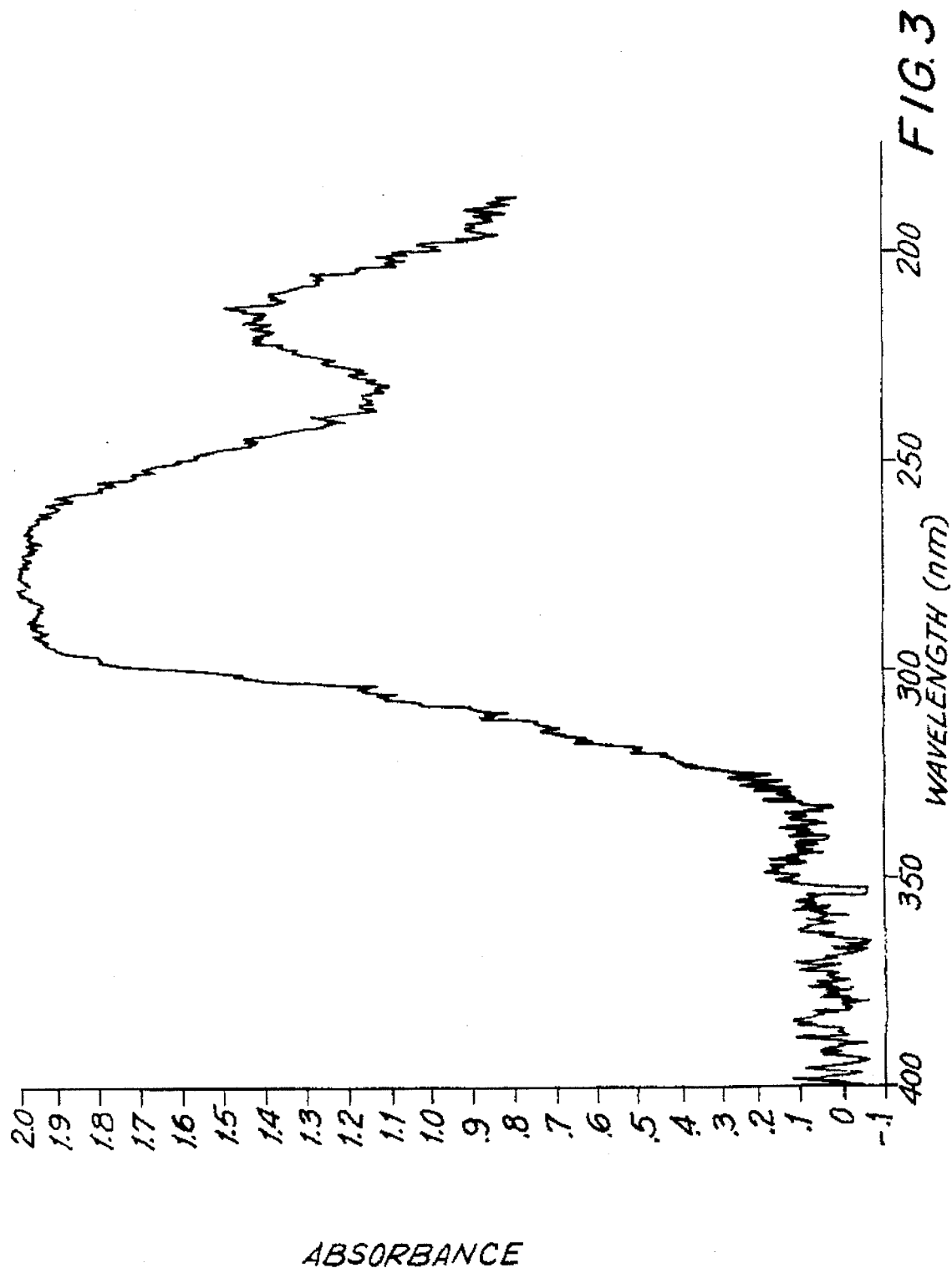
FIG. 3 is a spectral analysis of the solution of FIG. 2, after 30 seconds of exposure, showing peaks identifying 7-dehydrocholesterol, previtamin $D_3$ and byproducts such tachysterol.

After ten seconds exposure, the peak had begun to broaden on both sides. After 30 seconds, the distinct peaks observed were almost obliterated and the peak was clearly growing on the high energy side of the spectrum with not much change on the low energy side. This spectrum is shown in FIG. 3. From this point up to 4 min. the spectrum remained relatively constant and then started to decrease in size.

The absorption maximum for previtamin $D_3$ is at 260 nm while that of tachysterol, the undesirable side product, is at 280 nm. Even very early in the reaction the previtamin $D_3$ produced begins to be converted to tachysterol. After 30 to 60 sec. the predominate product is tachysterol. After about 4 min. the tachysterol is degraded by other photochemical side reactions.

EXAMPLE 2

Figure 4:
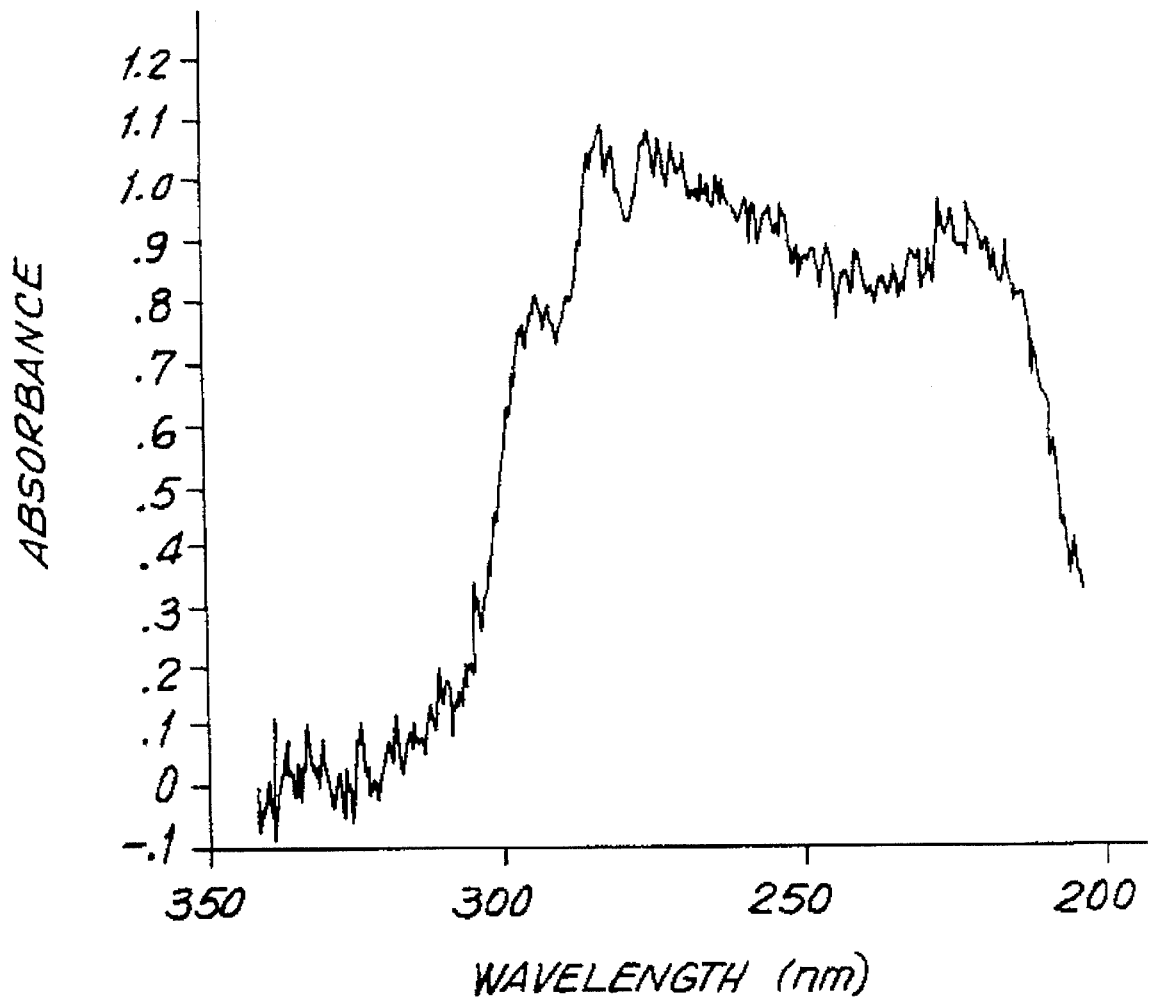
FIG. 4 is a spectral analysis of photolysis of 7-DHC in accordance with an embodiment of the invention showing peaks identifying 7-dehydrocholesterol and previtamin $D_3$.
Figure 5:
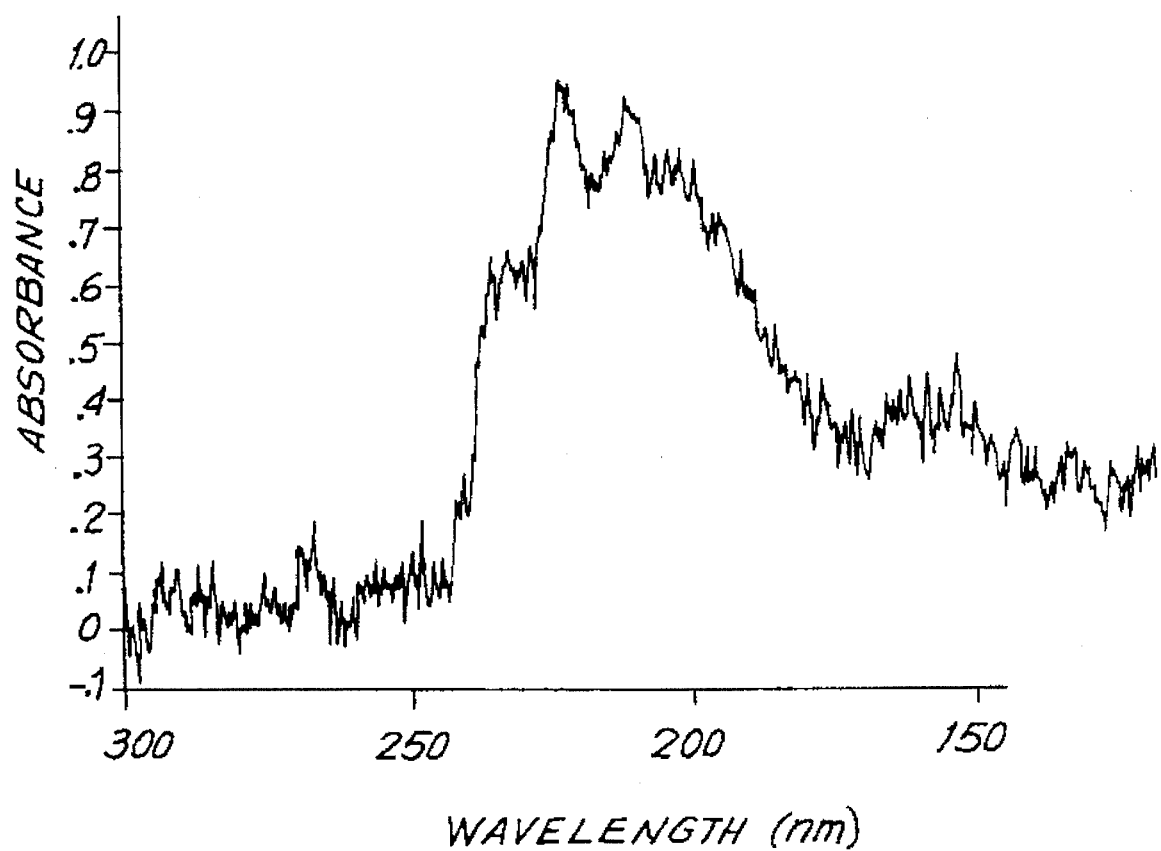
FIG. 5 is a spectral analysis of the material of FIG. 4, prior to exposure, showing peaks identifying 7-DHC.

To show that the percentage of desirable product can be increased by choosing a catalyst in accordance with the invention, Silica gel (Aldrich 21,447-7, 115–140 mesh) was loaded with 7-dehydrocholesterol from pentane solvent in a 2% by weight loading, without any pretreatment of the silica. The sample turned slightly gray after removal of solvent. An 11 mg sample of the loaded silica was put in a quartz glass reactor and the reactor was purged with nitrogen. The sample was then agitated and exposed from a low pressure mercury lamp for 10 min. The product mixture was extracted from the silica with methanol and a UV spectrum was taken (FIG. 4). The spectrum was compared to a spectrum of an 11 mg sample prior to exposure (FIG. 5). Although some starting material remained, there was a large absorption peak at 260 nm indicating significant formation of previtamin $D_3$. In addition, there was no evidence of absorption at 280 nm, showing that previtamin $D_3$ was not converted to tachysterol on silica as it is when the reaction is run in solution.

Examples 3 and 4 demonstrate the effect of adding water to the silica.

EXAMPLE 3

A sample of the silica gel was dried at 200° C. 0.81 g water was added to 2.8 g of the dried silica (29% water). The dried silica and wet silica were loaded to 2% with 7-dehydrocholesterol from a pentane solution. After removal of the pentane, the dried silica turned pink, while the wet silica remained white, indicating that there was no decomposition of 7-dehydrocholesterol in the wet silica. The latter sample was irradiated and worked up as described in Example 2. The results were similar to those of Example 2, with previtamin $D_3$ being the major product, but with the formation of a small amount of tachysterol.

EXAMPLE 4

Dried silica gel was loaded with water to a 7.5% water level and was treated as described in Example 3. The results were the same as in Example 3, both in the stability of 7-dehydrocholesterol on the silica and in the photolysis results.

Examples 5 and 6 demonstrate that the reaction can be run in both a rotating fluidized bed and in a gravity based fluidized bed photochemical reactor.

EXAMPLE 5

50 g of silica containing 15% water and loaded with 2% 7-dehydrocholesterol were put in a rotating fluidized bed reactor fit with a 5 watt low pressure mercury lamp. The bed was fluidized and the sample exposed for 128 min. The silica was slightly pink, suggesting that the dry nitrogen used for fluidization had removed some water from the sample. After workup, as in previous example, the UV spectrum showed significant conversion to previtamin $D_3$ and some formation of tachysterol.

EXAMPLE 6

2% of 7-dehydrocholesterol on silica containing 9% water was put in a cylindrical quartz gravity based fluidized bed. The sample was fluidized with dry nitrogen and exposed from outside of the bed with a low pressure mercury lamp. Samples were taken at different time intervals and worked up and analyzed as above. After 15 min., a significant amount of previtamin $D_3$ had been formed and very little tachysterol was present. After 60 min., previtamin $D_3$ was the most important peak in the spectrum and there was still no significant increase in tachysterol.

EXAMPLE 7

A 2% loading of 7-dehydrocholesterol in a Y zeolite with a Si:Al ratio of 2.5 in the sodium form (Tosoh HSZ-320NAA) was treated in the same way as the sample of Example 6. After 90 min. exposure, a significant amount of previtamin $D_3$ and very little tachysterol had been produced.

EXAMPLE 8

A 2% loading of 7-dehydrocholesterol on mordenite with a Si:Al ratio of 5.2–6 in the sodium form (Valfor C500-11 from PQ) was treated in the same was as in Example 6. After 120 min., a significant amount of previtamin $D_3$ was formed, but there was very little tachysterol formed.

EXAMPLES 9–16

Examples 9–16 follow the general procedures described above for loading, exposing, and extracting the products. They were analyzed by both UV and high performance liquid chromatography. Separations were carried out on Spherisorb 5 micron silica column, 250×4.6 mm. The mobile phase was a 70:30:2 mix of chloroform:hexane:ethyl acetate. The flow rate was 1.0 ml/min. The reaction conditions are given below in Table 1 and the results are given in Table 2.

TABLE 1

| REACTION CONDITIONS | | | |
| --- | --- | --- | --- |
| Exam. | Substrate | Exposure Time | Other Comments |
| 9 | Hexane Solution | 15 min. | Standard |
| 10 | Silica 60 Å pore | 120 | 1st extraction |

TABLE 1-continued

REACTION CONDITIONS

| Exam. | Substrate | Exposure Time | Other Comments |
|---|---|---|---|
| 11 | See example 10 | 120 | 2nd extraction of Ex. 10 |
| 12 | Silica 25 Å pore | 60 | |
| 13 | Silica 25 Å pore | 120 | |
| 14 | Na zeolite mordenite 7-8Å chambers | 120 | |
| 15 | Na Y-zeolite (15 Å supercages) | 90 | |
| 16 | Micelle | 10 | Hexadecyltrimethyl-ammonium Chloride |

TABLE 2

HPLC RESULTS

Relative Areas for Various Retention Time

| Example | 11.2 previtamin $D_3$ | 12.2 (tachysterol) | 13.7 | 15.5 (7-DHC) | ratio of 11.2:12.2 |
|---|---|---|---|---|---|
| 9 | 7.0 | 3.5 | 1.3 | 1 | 2.0 |
| 10 | 2.9 | 1 | 2.5 | 92 | 2.9 |
| 11 | 1 | 8.6 | 4.8 | 5.4 | 0.12 |
| 10 + 11[c] | 2.0 | 1 | 1.6 | 280 | 2.0 |
| 12 | 1 | NP | NP | 3.28 | large |
| 13 | 6.2 | 1 | 1.9 | 4.3 | 6.2 |
| 14 | 9.4 | NP | 1 | 32 | large |
| 15 | 1 | NP | NP | 16 | large |
| 16 | 1 | 21 | 11 | | 0.05 |

NP No peak observed
[c]Combined data

From the hexane data, it was concluded that the material eluted at 12.2 min is tachysterol. The size and kind of microreactor is important to the ratio of products formed. Where the microreactor is several times the size of the 7-DHC, the undesirable side reactions are more favored. For example the silica with 60 Å pores (Ex. 10 and 11) give a ratio of previtamin $D_3$:tachysterol similar to that of the reaction in hexane (Ex. 9). In micelles (Ex. 16), however, which form a similarly sized microreactor, but with an environment similar to that of a hydrocarbon solvent, tachysterol is very heavily favored.

In microreactors whose dimensions more closely approximate that of the steroidal skeleton, the reaction is much more preferentially controlled. Silica with 25 Å pores (Ex. 12), Zeolite-Y with about 15 Å supercages (Ex. 15), and zeolite mordenite with long channels with a diameter of 7–8 Å (Ex. 14) gave no observable tachysterol at 10 to 25% conversion. Even at higher conversions (Ex. 13), 7-DHC is still heavily favored. These results demonstrate the importance of the control of reaction space to the kinds of products obtained.

Accordingly, the method of the present invention employs microreactors to control the stereochemical direction of the photolysis of steroids such as 7-dehydrocholesterol or its analogues to yield previtamin $D_3$ or its analogues. 7-dehydrocholesterol is incorporated into the pores of silica or into the channels and chambers of zeolites and is irradiated to provide a very high yield of previtamin $D_3$ and relatively low yield of tachysterol, compared to the product ratios when the reaction is conducted in solution. Consequently, purification of the reaction product is simpler and waste of the reactant is minimized. Furthermore, the reaction steps involving multiple irradiations can be eliminated as can the use of sensitizers and initiators. Furthermore, previtamin $D_3$ can be converted to vitamin $D_3$ by thermal rearrangement while still on the solid substrate.

By sorbing reactant into microreactors selected to limit the formation of undesirable byproducts, conversion of from about 10 to 30% can be expected, with a ratio of desired product to byproduct greater than 5:1 and even reacting levels above 20:1 or above 100:1.

It will thus be seen that the objects set forth above, among those made apparent from the preceding description, are efficiently attained and, since certain changes may be made in carrying out the above method and in the constructions set forth without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

Particularly it is to be understood that in said claims, ingredients or compounds recited in the singular are intended to include compatible mixtures of such ingredients wherever the sense permits.

What is claimed is:

1. A method of conducting a chemical reaction of steroidal reactant compounds to yield a selected reaction product, comprising:

providing a catalyst formed with a plurality of microreactors having a reaction space selectively sized for favoring the production of the selected product, with an average diameter of less than about 30 Å;

introducing at least one steroidal reactant compound within the reaction space; and irradiating the reactant compound within the reaction space with radiation of a selected wavelength to photoconvert the reactant to a selected reaction product.

2. The method of claim 1, wherein the steroidal compound is 7-dehydrocholesterol and the reaction product is previtamin $D_3$.

3. The method of claim 1, wherein the reactants are selected so that the reaction product is a form of vitamin D.

4. The method of claim 1, wherein the catalyst is a solid particle having microreactors in the form of controlled spaces and the irradiation takes place in a fluidized bed reactor, while the catalyst is fluidized with a fluidizing gas.

5. The method of claim 1, wherein the catalyst is silica gel and including the step of wetting the silica gel prior to addition of the reactant.

6. The method of claim 4, wherein the fluidizing gas is humidified to control the water content of the catalyst and reactant.

7. The method of claim 3, wherein the temperature during irradiation is maintained at between −30° C. and 30° C.

8. The method of claim 3, wherein the temperature of the catalyst and reactant during irradiation is maintained at between 0° C. and 20° C.

9. The method of claim 4, wherein the temperature of the fluidizing gas is selectively varied to thermally initiate reactions.

10. The method of claim 1, wherein the steroid reactant structure has a double bond in the 5, 6 and 7, 8 positions.

11. The method of claim 1, wherein the steroid reactant has an oxygen substituent on the 3-position.

12. The method of claim 1, wherein the catalyst and reactant is irradiated with light in the range of 200 to 700 nm.

13. The method of claim 3, wherein the catalyst and reactant is irradiated with light having a wavelength between about 200 and 300 nm.

14. The method of claim 1, wherein the catalyst includes solid particles having reaction spaces therein and the reactant is sorbed into the reaction spaces of the solid catalyst particles and the catalyst particles have a particle diameter in the range of from about 0.1 to 500 μm.

15. The method of claim 14, wherein the particle diameter is in the range of about 1–200 μm.

16. The method of claim 1, wherein the catalyst includes solid catalyst particles and the steroidal reactant compound is combined with a solvent and loaded from the solvent into the reactions spaces of the solid catalyst particles.

17. The method of claim 16, wherein the solvent is a hydrocarbon organic solvent.

18. The method of claim 1, including the step of removing the reaction product from the catalyst with a solvent.

19. The method of claim 1, wherein the solid catalyst particles include zeolitic material.

20. The method of claim 19, wherein the zeolitic material includes channels having a diameter of about 6–8 Å.

21. The method of claim 20, wherein the zeolitic material includes chambers having a diameter of about 12–16 Å.

22. The method of claim 1, wherein the catalyst includes silica material.

23. The method of claim 22, wherein the silica has a pore size of from about 20 to 30 Å in diameter.

24. A method of producing previtamin $D_3$, comprising combining 7-dehydrocholesterol reactant with a microreactor selected from the group consisting of silica material and zeolitic material having a controlled reaction space less than about 30 Å in diameter; irradiating the microreactor with the reactant therein with light of a selected wavelength for initiating a photoconversion of the reactant; and permitting the 7-dehydrocholesterol to convert to previtamin $D_3$.

25. The method of claim 24, including converting the previtamin $D_3$ into a form of Vitamin $D_3$.

26. The method of claim 24, wherein the conversion of reactant is over 10% and the ratio of product to reactant is over 5:1.

27. The method of claim 26, wherein the ratio of product to reactant is over 20:1.

* * * * *